US010022490B2

(12) United States Patent
Blankenship et al.

(10) Patent No.: US 10,022,490 B2
(45) Date of Patent: Jul. 17, 2018

(54) TRANSFORMABLE INTRAVENOUS POLE AND BOOM COMBINATION AND METHOD THEREOF

(71) Applicant: Skytron, LLC, Grand Rapids, MI (US)

(72) Inventors: Peter B. Blankenship, Anoka, MN (US); Samuel A. Blankenship, Anoka, MN (US)

(73) Assignee: Skytron, LLC, Grand Rapids, MI (US)

( * ) Notice: Subject to any disclaimer, the term of this patent is extended or adjusted under 35 U.S.C. 154(b) by 0 days.

(21) Appl. No.: 15/624,174

(22) Filed: Jun. 15, 2017

(65) Prior Publication Data

US 2017/0281856 A1    Oct. 5, 2017

Related U.S. Application Data

(63) Continuation of application No. 14/853,188, filed on Sep. 14, 2015, now Pat. No. 9,707,334, which is a continuation-in-part of application No. PCT/US2014/029213, filed on Mar. 14, 2014.

(60) Provisional application No. 62/207,106, filed on Aug. 19, 2015, provisional application No. 62/148,398, filed on Apr. 16, 2015, provisional application No. 61/788,094, filed on Mar. 15, 2013.

(51) Int. Cl.
| F16M 11/00 | (2006.01) |
| A61M 5/14 | (2006.01) |
| F16M 13/02 | (2006.01) |
| F16M 11/42 | (2006.01) |

(52) U.S. Cl.
CPC .......... *A61M 5/1415* (2013.01); *F16M 11/42* (2013.01); *F16M 13/022* (2013.01); *A61M 2207/00* (2013.01); *A61M 2209/082* (2013.01); *A61M 2209/084* (2013.01)

(58) Field of Classification Search
CPC .. F16M 7/00; F16M 2200/02; F16M 2200/04; F16M 2200/066; F16M 11/02; F16M 11/425; F16M 13/005; F16M 2200/025; F16M 11/2028; F16M 11/2071; F16M 2200/061; F16M 11/205; F16M 11/2057; F16M 13/06; F16M 11/121; F16M 11/2007
USPC .... 248/125.8, 128, 129, 168, 169, 170, 171, 248/434, 435, 188.1, 188.6, 188.8
See application file for complete search history.

(56) References Cited

U.S. PATENT DOCUMENTS

| 5,319,816 A | 6/1994 | Ruehl |
| 6,019,484 A | 2/2000 | Seyler |
| 6,430,761 B1 | 8/2002 | Brandorff et al. |
| 7,216,382 B2 | 5/2007 | Newkirk et al. |

(Continued)

OTHER PUBLICATIONS

International Search Report corresponding to International Patent Application No. PCT/US2014/029213 (2 pages) (dated Jul. 30, 2014).

*Primary Examiner* — Steven M Marsh
(74) *Attorney, Agent, or Firm* — Warner Norcross + Judd LLP (57) ABSTRACT

An intravenous (IV) pole docking system for supporting medical equipment having a mast engaged to a base, the base having legs to support the mast and a lifting mechanism engaged to the base and the mast for moving the base along the mast in combination with an extension arm meant to reduce the IV pole footprint. The boom/IV pole system can reduce excess obstacles in and around hospital bed, surgical rooms and the like.

17 Claims, 6 Drawing Sheets

(56) References Cited

U.S. PATENT DOCUMENTS

| | | | |
|---|---|---|---|
| 7,428,759 B2 * | 9/2008 | Bain | A61G 7/1017 212/294 |
| 7,865,983 B2 | 1/2011 | Newkirk et al. | |
| 7,918,422 B2 | 4/2011 | Blankenship et al. | |
| 8,100,371 B2 | 1/2012 | Eggleston et al. | |
| 2007/0023587 A1 | 2/2007 | Eggleston et al. | |
| 2007/0267551 A1 | 11/2007 | Townsend | |
| 2008/0283692 A1 | 11/2008 | Leinen | |
| 2009/0321589 A1 | 12/2009 | Hampton et al. | |
| 2012/0090090 A1 | 4/2012 | Aabakken | |
| 2013/0181100 A1 | 7/2013 | Blankenship et al. | |

* cited by examiner

TRANSFORMABLE INTRAVENOUS POLE AND BOOM COMBINATION AND METHOD THEREOF

RELATED APPLICATIONS

This application is a continuation of U.S. patent application Ser. No. 14/853,188, filed Sep. 14, 2015, which is a continuation-in-part of PCT/US2014/029213, filed Mar. 14, 2014, which claims priority to U.S. Provisional Application Ser. No. 61/788,094, filed Mar. 15, 2013, and also claims priority directly to U.S. Provisional Application Ser. No. 62/148,398 filed Apr. 16, 2015, and U.S. Provisional Application Ser. No. 62/207,106 filed Aug. 19, 2015, the contents of which are hereby incorporated by reference as if recited in full herein.

BACKGROUND

For many years, patients needing intravenous (IV) fluid transfusions have been moved by a patient transportation apparatus such as a wheelchair, wheeled bed, stretcher, gurney or the like while receiving intravenous (IV) transfusions by the use of mobile IV poles. These IV poles, however, suffer from a number of drawbacks.

One unsatisfactory form of a mobile IV pole is a pole permanently attached to, and using out of, the patient transportation device such as that described in published US Patent Application 2006/0243500A1. This form imposes significant burdens on hospital staff as each time the patient is moved, pumps and fluid bags must both be transferred onto the transportation device before the patient is moved, and then again the pumps and fluid bags must be transferred off of the transportation device once the patient arrives at their destination. The repeated transfer of bags and pumps increases the risks of bags or pumps being dropped leading to wasted medicines needing replacement and wasted environmental services cleaning up spills as well as damage occurring to expensive pumps and equipment. Similarly, the permanently attached pole makes the patient transportation device bulky causing awkward and difficult movement, storage, and maintenance. In the case of beds, permanently attached poles render the beds particularly bulky, and difficult to maneuver and difficulty in linen changes. Further, beds with poles significantly increase the difficulty of patient transfer into and out of the bed. Most seriously of all, constant removal and re-attachment of IV bags and pumps increases the risks of IV leads being strained or pulled entirely from the patient's body, complicating a patient's treatment and potentially putting the individual at risk of infection or improper treatment.

Another unsatisfactory form of mobile IV pole is a free standing wheeled pole that is moved alongside the patient transfer apparatus such as that described in published US Patent Application 2006/0222341A1. This device unfortunately also imposes significant burdens on hospital staff. In this device one hand must be used to push the patient transfer apparatus and another to simultaneously move the IV pole. Because patient transfer apparatuses may be heavy, and not designed for one handed pushing, repeatedly utilizing one person to simultaneously move both the pole and the transfer apparatus causing significant strain, and often results in back and sprain injuries in medical personnel. Also, such pushing increases the risk of injury to a patient in that the pole may tip over onto the patient or that the patient transfer apparatus may strike walls or objects and aggravate an injury. The alternative of utilizing multiple medical personnel to transport a single patient is inefficient and cost prohibitive in an era of scarce nurses and other medical personnel.

For at least these reasons there is a need for an improved IV pole system. Additional details of the summarized embodiments of the invention and/or additional embodiments of the invention may be found in the Detailed Description below.

SUMMARY

The invention generally relates to a boom with an IV pole docking system for supporting medical equipment comprising a base, a mast and a lifting mechanism.

In one example embodiment, the IV pole is constructed and arranged to position a plurality of legs in either an extended configuration and in a retracted configuration. In the example embodiment, the IV pole system includes an extension arm which can be moved around and over a bed, chair or patient holding apparatus to allow a reduced "footprint," thus improving health care professional safety. In another example embodiment, a method is provided of retracting and extending an IV pole system using an extension arm.

This and other aspects of the invention are described in more detail in the accompanying description and drawings.

BRIEF DESCRIPTION OF THE DRAWINGS

The invention is best understood from the following detailed description when read in connection with accompanying drawings, in which.

DETAILED DESCRIPTION

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 40, 90', 90", 90'").

In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art. The term "Fig." (whether in all capital letters or not) is used interchangeably with the word "Figure" as an abbreviation thereof in the specification and drawings. In the figures, certain layers, components or features may be exaggerated for clarity, and broken lines illustrate optional features or operations unless specified otherwise. In addition, the sequence of operations (or steps) is not limited to the order presented in the claims unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "bottom", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass orientations of above, below and behind. The device may be otherwise oriented (rotated 90° or at other orientations) and the spatially relative descriptors used herein interpreted accordingly.

The term "about" refers to numbers in a range of +/−20% of the noted value.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

The terms "accessory" and "accessory devices" refer to any clinical or hospital device that may be desirable to be provided for and/or moved with a patient including poles such as IV poles, monitor supports, tables, trays, pump supports, oxygen tank/canisters and the like.

The term "boom" refers to a support structure that is attached to structure of a room, typically suspended from the ceiling, and intended to organize and support hospital utility services (e.g., electricity, gas) and/or medical devices.

Figure 1:
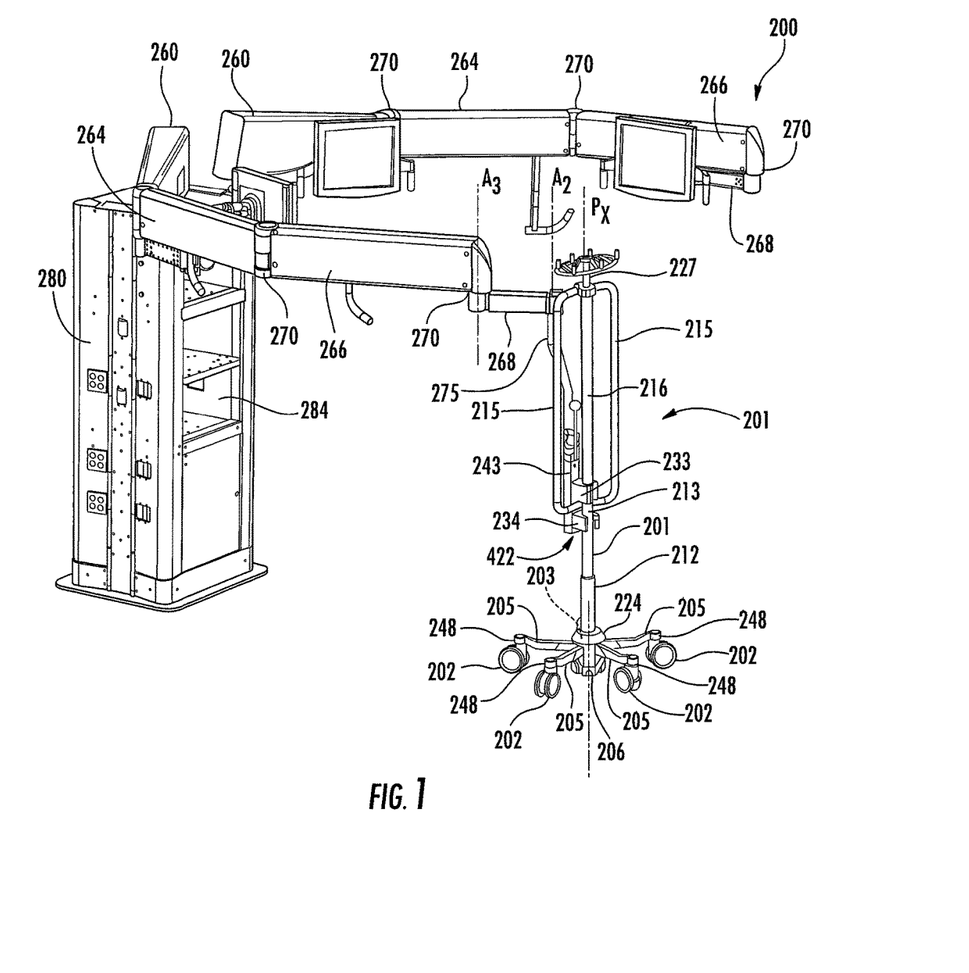
FIG. 1 is a perspective view of a self retracting IV pole in the expanded configuration mounted on an extension arm.

Referring now to FIG. 1, in this example embodiment there is a boom with a docking system (200) for a retractable IV pole (201) in which a plurality of legs (205) of the IV pole (201) are in an expanded/extended position. A lifting mechanism allows for non-user powered retraction of a base (224) of an IV pole (201). In at least one embodiment, the IV pole (201) comprises a base (224) which can stabilize the IV pole (201), a top (227) where equipment can be hung, and a main mast (216) extending between base (224) and top (227). FIG. 1 shows the IV pole (201) in an expanded configuration.

Figure 3:
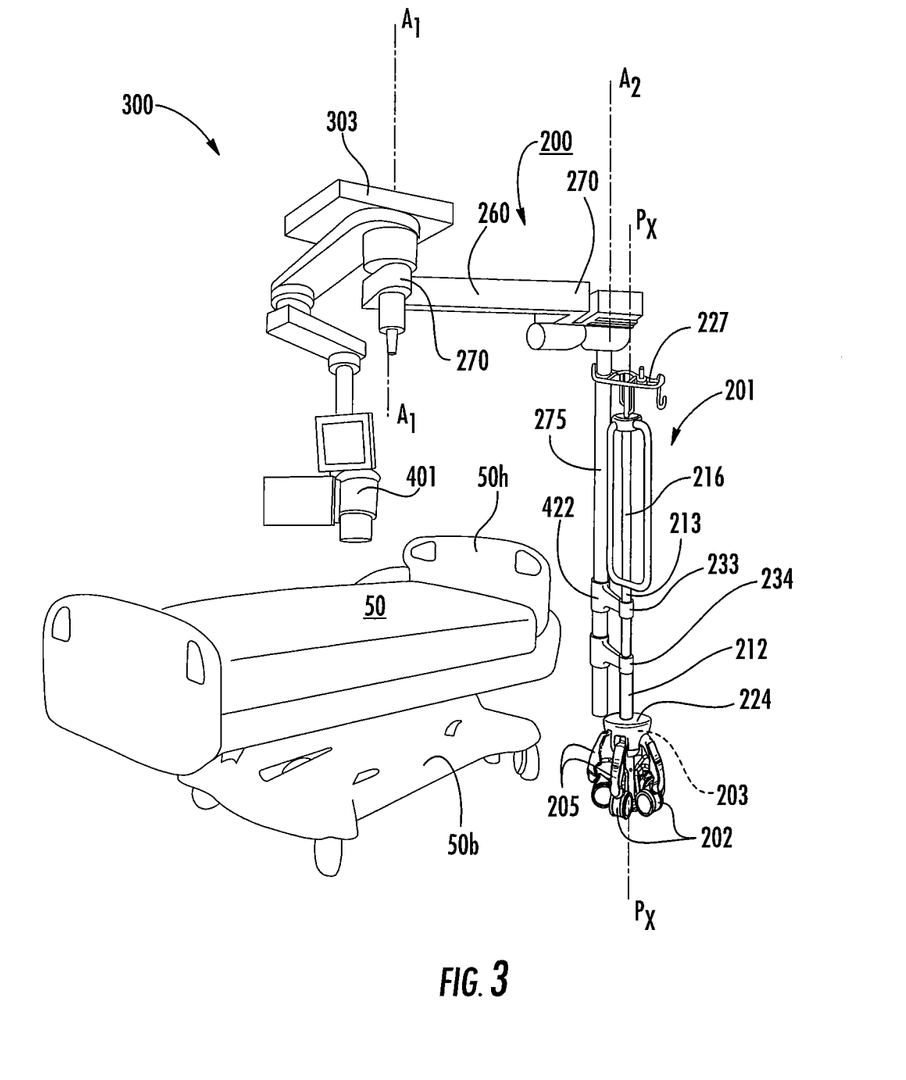
FIG. 3 is a side perspective view of a pole in a retracted configuration, docked to booms and/or column mounts in a hospital or clinic room according to embodiments of the present invention.

In FIG. 1, the boom and IV pole system (200) shows the IV pole (201) can be releasably engaged to an extension arm (260) which attaches to mast (216) via at least one laterally extending attachment member (233), shown as upper and lower attachment members (233), (234). The attachment members (233), (234) can be held on a bracket such as a mount plate (243) (FIG. 1) attached to the extension arm (260) or directly on the extension arm (260) (FIG. 3).

Attached at or near the end of each leg (205) is at least one wheel or rolling device (202). In at least one embodiment, the wheels are caster-type wheels capable of freely rotating along a leg-wheel connection (248). Although in this particular depiction there are five legs (205) (4 clearly shown) with five four-inch caster-type wheels (202) (4 shown), embodiments with different numbers of legs (205) (such as 1, 2, 3 or more) and different sized or types of wheels (202) are within the scope of the invention.

In this example embodiment, base (224) of IV pole system (200) comprises two or more legs (205) which are pivotably engaged to IV pole (200) by leg connections. The leg connections can be pins, screws, nuts or any other pivoting engagement known in the art. When in the expanded state legs (205) are pivoted to extend away from mast (216) of IV pole system (200) to provide a stable support platform. When in the retracted state, shown in FIG. 2, legs (205) are pivoted inwards towards mast (216) of IV pole system (200) allowing IV pole system (200) to be moved with a reduced diameter. In a related embodiment, leg (205) can retract upwards towards the mast.

Figure 2:
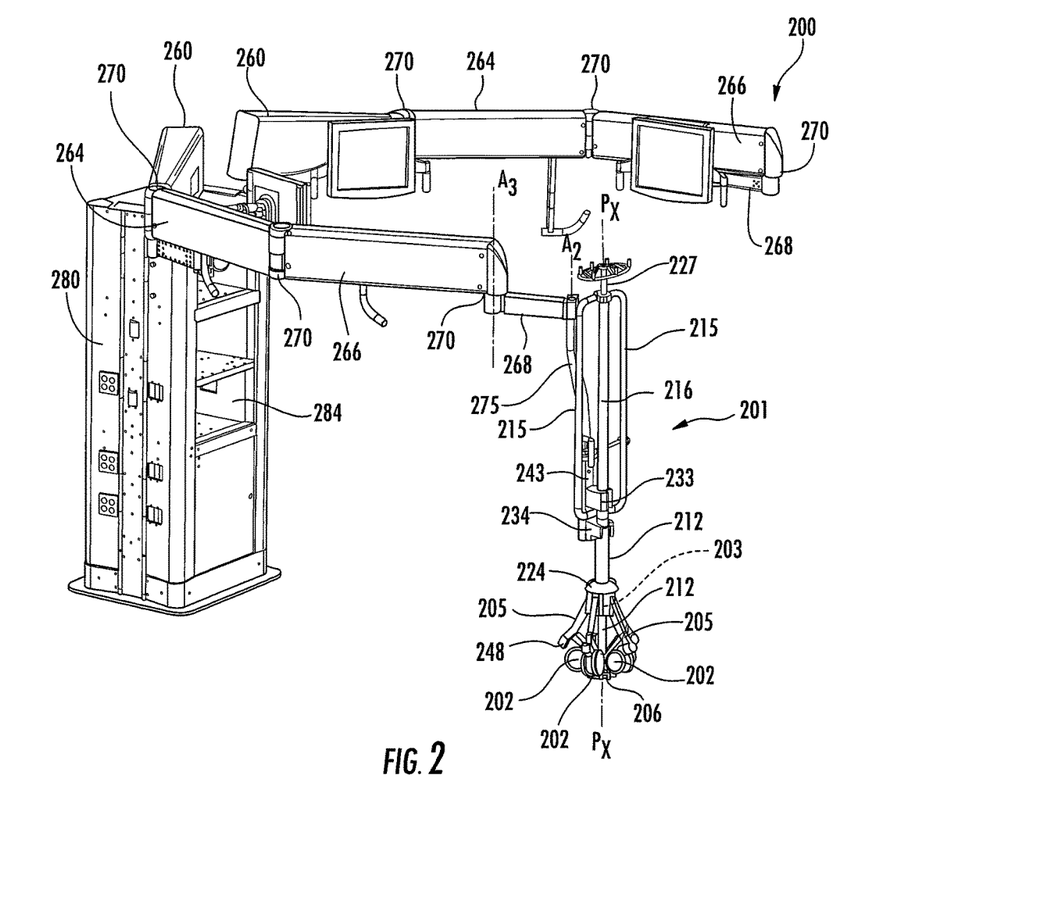
FIG. 2 is a perspective view of a self retracting IV pole in the retracted configuration mounted on an extension arm.

Referring now to FIG. 2, there is shown an embodiment of base (224) of IV pole system (200). A lifting mechanism (203) may be used to retract and expand base (224). One particular lifting mechanism is a gas spring which are well known in the art and are described at least in U.S. Pat. Nos. 7,222,702, 7,073,642, and 4,582,304, all of which are incorporated by reference in their entirety.

In at least one embodiment, IV pole system (200) comprises a base support (206) located at or near the bottom of mast (212). In at least one embodiment, base support (206) is positioned around a portion of mast (212). Base support (206) is one location where leg (205) is pivotably engaged to the IV pole by at least one leg connection (210). As the lifting mechanism initiates the movement of base support (206) upward, the portion of leg (205) near a leg connection (210) is also moved upwards. This upward movement in turn rotates the portion of the leg-wheel connection where the wheel (202) is engaged to the leg (205) into a position closer to the mast (212).

In at least one embodiment, lifting mechanism is integrally related to the base support (206). Some or all of base support (206) can be surrounded at least in part by a housing, which may contain all, or some, of the components which may facilitate the actuation of lifting mechanism. In at least one embodiment, the housing may also comprise a hygienic fluid and tight seal to prevent the entry of liquids, blood, organic matter or other material into the interior of base (224) which may drip or splatter against IV pole system (200) during use.

Referring still to FIGS. 1 and 2, extension arm (260) includes a first segment (264), a second segment (266) and a third segment (268). Extension arm (260) can directly or indirectly support a downwardly extending arm (275) which may include at least one pole attachment device (422), shown comprising a mount plate (243) with mounts (233) and (234). Extension segments (264, 266 and 268), may be made of materials know to those skilled in the art. In one example embodiment, the extension arm segments (264), (266), (268) comprise a metal paneling exterior. The metal can preferably be rust resistant and not substantially degrade with the use of antimicrobial and disinfectant cleaners, as commonly used in a hospital, nursing home or operating room environments.

Extension arm (260) can attach to a central work station (280) that is configured to be installed into an operating room. The one or more extension arms supported by the central work station (280) may be configured to extend over, for example, an operating table in the operating room. The central work station (280) can include one or more bays (284) configured to receive a modular rack of electrical equipment. In particular embodiments, the central work station (280) can be designed to accommodate modular equipment and utility racks that include video processing, computer, and electronic equipment, and other utility equipment that can be easy inserted and removed from central work station (280). In some embodiments, laterally extending arm (260) can be attached to a wall in the room or hallway (directly or via a bracket assembly).

In various embodiments, cabinets of the central work station (280) can further incorporate wiring to connect the equipment installed in the modular racks to video monitors and other equipment mounted on extension arm (260). The modular racks may be preconfigured with a variety of electronic equipment such as computers, video processors and the like.

The central work station (280) can optionally provide electrical outlets for IV pumps, screens and other known health care monitors. First segment (264) and second segment (266) can be coupled with a rotating pivot joint (270) that allows for (e.g., rotational and/or horizontal) movement of the extension arm (260) to a desired position. Similarly second segment (266) and third segment (268) can also be connected in a similar manner. It should be appreciated that third segment (268) may comprise a vertical arm (275).

In some embodiments, the boom with IV pole docking system (200) can comprise at least first and second pole attachment mounts, one being an upper mount (233) and one being a lower mount (234). In at least one embodiment, IV pole (201) can have a narrower segment or portion (213) of the main mast (212) releasably engaged to the upper mount (233). In at least one embodiment, one or more of the mounts have a generally rounded interior cavity/channel with an open side facing the IV pole (201). In some embodiments, at least one of the two mounts can be a clip which is a biased gripping member (such as a strip of bent metal). All appropriate gripping, clamping, holding or other attachment configurations known in the art may be useful for the at least one pole attachment member (422).

IV pole system (200) can be wheeled towards mounts (233), (234) and a narrow portion (213) can slide within or adjacent to upper mount (233). In at least one embodiment, one or more supplemental masts or wings (215) descend lower than narrow portion (213) allowing for the option to place equipment on wings (215) in a lower position when compared to equipment placed on main mast (216). In at least one embodiment, portions above and below narrow portion (213) can widen to the width of main mast (216). These different shaped/size portions, e.g., tapered and/or stepped portions allow IV pole system (200) to be positioned above or below mounts (233), (234) and appropriately drop or ascend into proper position. Use of changes in outer wall dimensions, e.g., tapered or stepped, pole portions can also allow the user to secure IV pole system (200) to mounts (233), (234) without needing to perfectly align narrow portion (213) with pole mounts (233, 234).

Main mast (216) can be supported by the boom docking system pole mounts (233, 234) and in at least one embodiment, upper mount (233) can be constructed and arranged to grasp the diameter of narrow portion (213) of main mast (216). In at least one embodiment, lower mount (234), where used, can be constructed and arranged to grasp the diameter of the bottom of mast (212) or base sleeve. In at least one embodiment, lower mount (234) has a clip or clamp or other portion sized to grasp the diameter of mast (212) or base sleeve. Mount (233), (234) may also include a mechanism to adjust the height of the mount. This adjustment device can be configured to allow the IV pole (201) to be easily coupled with at least one of the mounts (233) and/or (234).

In at least one embodiment, IV pole system (200) is suspended in the air or at least supported prior to engaging lifting mechanism. By suspending or supporting IV pole system (200) prior to actuation, at least some of the weight of IV Pole system (200), is removed from the wheels (202) which facilitates a more efficient retraction of legs (205) of IV pole system (200). In a related embodiment, the weight is relieved by rolling IV Pole system (200) into at least one or more mounts (233), (234) which lift IV pole system (200) and bear the weight of IV pole system (200) and equipment.

In at least one embodiment, IV pole (201) comprises an internal spring that applies continuous pressure on the legs prior to engaging lifting mechanism. The internal spring that applies continuous pressure on the legs is not required.

In some embodiments, some of the weight of IV pole (201) is removed from the wheels (202) which facilitates a more efficient retraction of legs (205) of IV pole system (200). The IV pole system (200) base support (206) is positioned above the ground surface and act as the support mechanism when IV support system (200) is not engaged in a boom docking member.

In some embodiments, the weight of the IV pole (201) may be relieved by rolling IV pole system (201) into one or more mounts (233), (234) which lift IV pole (201) and bears the weight of IV pole (201) and any equipment held by the IV pole (201).

Referring now to FIG. 2, when or after IV pole (201) engages mounts (233), (234), the operator presses lifting mechanism, being in mechanical communication with base support (206), and raises legs (205) off the ground. Lifting IV pole system (200) off the ground reduces or eliminates any hysteresis effects and assures that lifting mechanism (203) easily retracts legs (205).

In at least one embodiment, mounts (234), (233) are movably engaged in communication with a downwardly extending arm (275) to allow for movement around the bed. This movement may be important when maneuvering an IV pole system (200) through tight areas such as, but not limited to, operating rooms or hospital rooms. In order to allow for a smooth 180 degree rotation around the bed, central work station (280) can be positioned about a perimeter of a hospital bed (50) (FIG. 3) or surgical table.

In some embodiments, a IV pole docking system (500) can be integrally mounted directly to at least one of a hospital bed (50) (FIG. 5A) and patient transportation device (e.g., wheelchair) to allow the IV pole (201) to be interchangeably mounted to the bed, typically a base of the bed (50b) (FIG. 3, 5A) via the bed docking system (500) (and/or transportation device) or the boom/pole docking system (200).

FIG. 3 illustrates an IV pole (201) that can dock to a tower or vertical extension arm (275) of a boom (300) in a medical room, such as a hospital room, a surgical room, and/or a diagnostic room. The boom (300) can optionally also hold diagnostic equipment such as CT or X-ray equipment (401).

The boom (300) can be mounted in any suitable manner such as ceiling, floor and/or wall mounted. As shown in FIG. 3, the boom (300) can be ceiling mounted and can support and/or be in communication with the downwardly extending arm (260) with the at least one pole attachment member (422).

The boom (300) can include a ceiling fixture support system (303) with one or more laterally extending movable arms (260) that directly or indirectly holds the downwardly extending support arm (275). The arm (275) can be configured as a single support arm for a respective IV pole (201). The arm (275) can rotate about a vertical axis $A_2$ and may allow vertical up and down movement. The laterally extending arm (260) may rotate about a vertical axis $A_1$ that is laterally spaced apart from the arm axis $A_2$. The laterally extending arm (260) and downwardly extending arm (275) can be attached via a joint (270) that allows rotation of one or both of the arms (260), (275) about another vertical axis $A_3$ that can reside laterally between axis $A_1$ and axis $A_2$.

The downwardly extending arm (275) can be telescoping to be able to change length or may be stationary. The downwardly extending arm (275) can be curvilinear. The arm (275) can extend laterally a distance away from the pole axis Px as the arm (275) rises toward the ceiling or boom support (303).

The boom (300) may include medical gas outlets, vacuum inlets, electric power outlets, communication systems, medical device support brackets, and attachments such as suction canisters and intravenous solution hangers. Ceiling-mounted facility booms (300) can be particularly suitable for operating rooms, intensive care units, emergency rooms, and other healthcare areas. The boom (300) can be a dedicated in-room boom intended to support operating microscopes or other surgical or diagnostic devices.

The boom (300), which can sometimes also be interchangeably referred to as a "tower", can include the at least one laterally extending pole attachment member (422). The at least one pole attachment member (422) can remain on the arm (275) or move with the pole (201) when disengaged and the wheels (202) on the ground and extended to support the pole (201). Where more than one pole attachment member (422) is used, e.g., members (233), (234), one can remain on the arm (275) of the boom (300) and another can travel with the pole (201), both can travel attached to the pole (201), or both can stay attached to the arm (275) of the boom (300).

The at least one pole attachment member (422) can be adjustable in length (e.g., laterally adjustable) and/or in diameter for holding (enclosing or partially surrounding) a pole segment of the pole (201).

The pole (201) can have a main mast (216) that merges into a lower tube (212) above the base (224). The mast (216) can have a smaller diameter relative to arm (260) of the boom (300) and/or the lower tube (212). The at least one pole attachment member (422) can allow the pole (201) to pivot or rotate relative to the boom (300) and may also optionally telescope or extend to allow for lateral spacing adjustment which may allow for better positioning of certain accessories relative to a patient, e.g., an oxygen tank, for example.

The pole (201) can have a different configuration than shown, including a different transformable pole configuration with different numbers of wheels/casters, different size wheels/casters and a different lift and/or wheel-extend lever and mechanism.

Figure 4A:
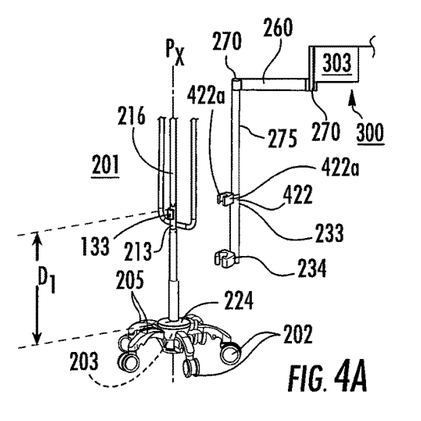
FIGS. 4A-4F are sequential views of examples of an exemplary boom-pole engagement interactions of a boom-pole docking system according to embodiments of the present invention.
Figure 4B:
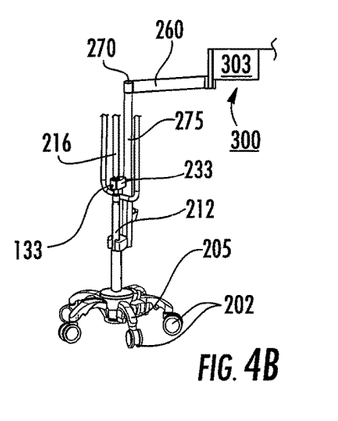
Figure 4C:
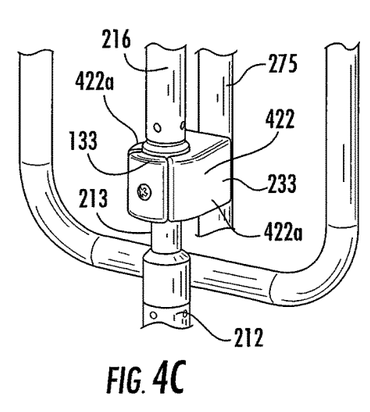
Figure 4D:
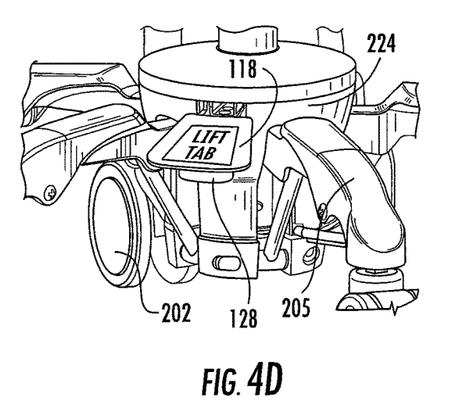
Figure 4E:
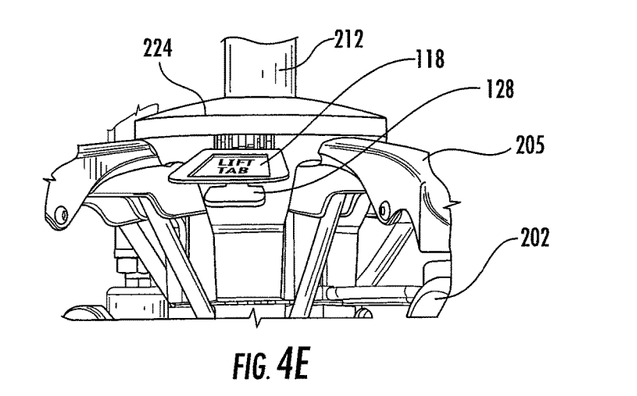
Figure 4F:
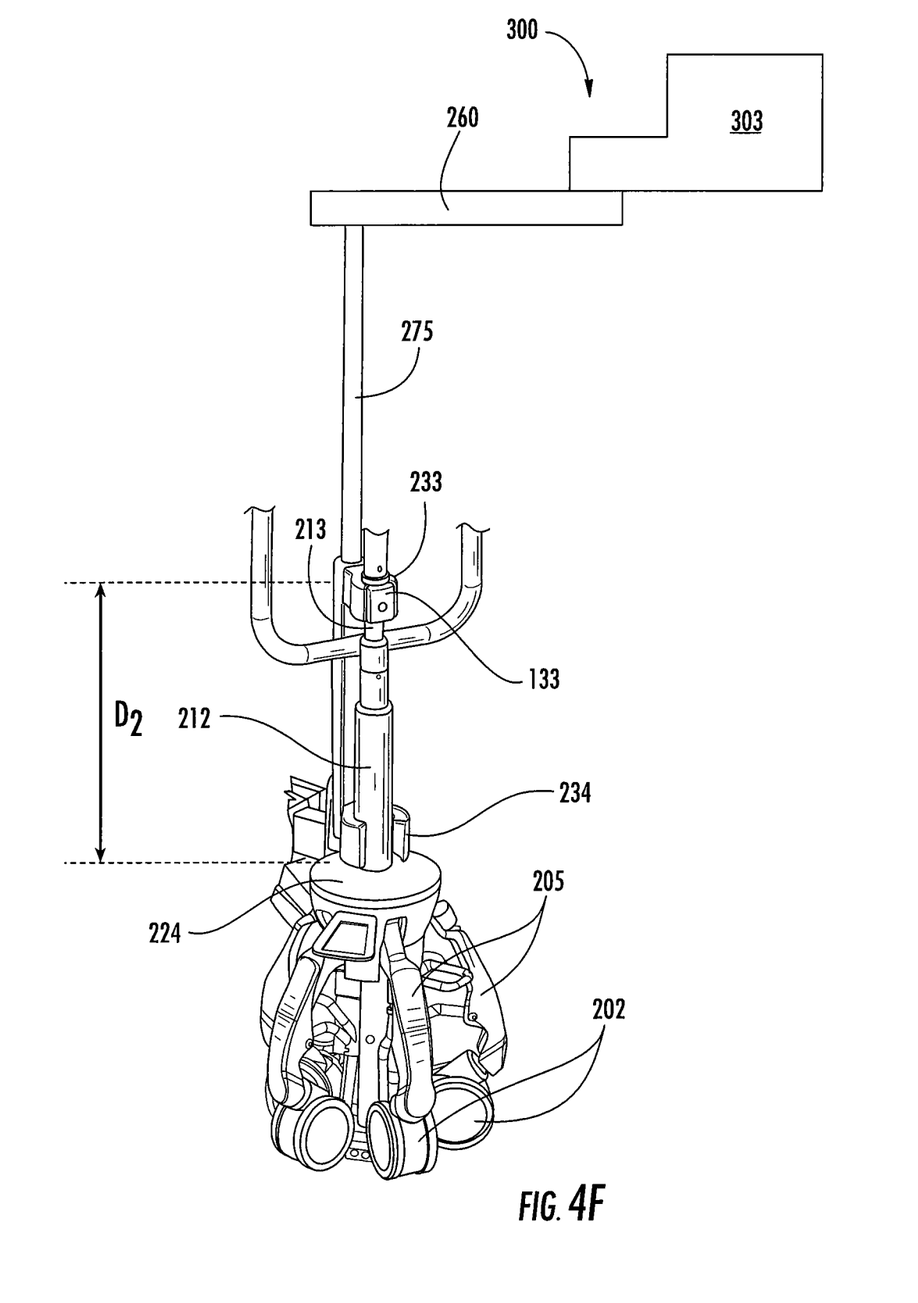

FIGS. 4A and 4F illustrate exemplary extended and retracted (suspended) configurations, respectively, of the pole (201). As shown, the base (224) can rise relative to the mast (216) to reside closer to the mast (216) or upper end of the pole (201) when attached to the at least one pole attachment member (422) and held, suspended by the boom (300), such that the legs (205) are retracted with the wheels (202) off the ground.

FIG. 4A-4F illustrate that the pole (201) can have a medial segment that has a smaller cross-section (213) (diameter) relative to adjacent upper and lower segments (216), (212), respectively. The smaller medial segment (213) can hold an outwardly facing key (133). As shown, the key (133) extends radially outward a distance from the medial segment (213) of the pole (201) for a circumferential distance. The radially extending distance can be between about 0.1 inch and 2 inches, typically between about 0.25 inches and 1 inch, in some embodiments. The key (133) can have an arcuate profile. The key (133) can extend circumferentially between about 30-60 degrees in some embodiments. The key (133) can be configured to engage and align with outwardly extending arms (422a) of the respective pole attachment member (422), shown as the upper pole attachment member (233). The key (133) can abut the end portions of each of the arms (422a) when in position. Other pole attachment configurations maybe used. The key (133) can reside a distance D1 away from the base (224) in the extended position with the wheels (202) on the floor as shown in FIG. 4A and a shorter distance D2 when the legs are raised with the wheels (202) off the floor when the IV pole (201) is suspended on the boom (300) as shown in FIG. 4F.

FIG. 4A-4F also illustrate a sequence of actions that can be used to dock a pole (201) to a boom (300) according to some embodiments. A user can roll the IV pole (210) into position, adjacent the arm (275) of the boom (300) and attach the pole (201) to the at least one pole attachment member (422). In some embodiments, as or after a user rolls the pole (201) into position, the pole (201) can be rotated to align the key (133) to reside adjacent the arms (422a) with the pole (213) held inside the arms (422a) and the key (133) facing outward. Once the pole (201) is aligned with the key (133) facing outward, the pole (201) can be pushed and into engagement with the pole mount (422). Proper (locking) engagement may be indicated by an audible "click".

The pole (201) can have a base (224) as discussed above. The base (224) can have an outwardly extending leg release safety cover (118) that can be lifted, typically with the top of a foot of a user. Only when the IV pole (201) is "clicked" into place can a user then access the lift pedal (128) to manually push down on the leg lift pedal (128). The leg lift pedal (128) may be in red or have red marking or other visual indicia noting care should be taken when engaging the lift mechanism using the lift pedal (128).

In some embodiments, the pole (201) can be configured to automatically retract the legs (205) and raise the wheels (202) off the floor, and also optionally self-lock to the arm (275) of the boom (300), all based on a single user action to initiate the automatic retracting and raising and, typically, the self-locking. Thus, a user can align the IV pole (201) with the arm (275) with the at least one pole attachment member (422) (e.g., boom adapter). The release pedal (128) on the IV pole (201) can be released (typically manually pushed down using a user's foot) to activate an upward movement of the legs (205). As the legs (205) rise, the legs (205) lose contact with the ground/floor and the pole (201) is suspended on the arm (275). The IV stand/pole (201) can self-lock into the boom adapter/pole attachment member(s) (422) (e.g., 233, 234) as the legs (205) continue to rise. The mast (216) that rises with the legs (205) can be larger than the opening for engaging the pole (201), locking the IV stand/pole (201) into the attachment member(s) (422) (i.e., boom adapter). The lifting of the legs (205) and self-locking engagement of the IV pole (201) to the boom (300) can thus be carried out simply by a single user action, the release of the IV pole (201) pedal. This can be referred to as a "one-touch" lift and lock actuation system to suspend the pole (201) to the boom arm (275).

In some embodiments, only the legs (205) rising upward with the associated lower pole segment also concurrently rising through the lower pole mount (234) locks the pole (201) in place on the boom arm (275), in response to the single-action pedal engagement by a user to lift and lock the pole (201) to the boom arm (275).

The self-locking can be carried out based on the lower attachment member (234) abutting the base (224) as the legs (205) are translated inward and upward to lift the wheels (202) (compare, for example, FIG. 4A with FIG. 4F). The pole segment (213) with the key (133) can be stationary as the base (224) rises upward.

Figure 5A:
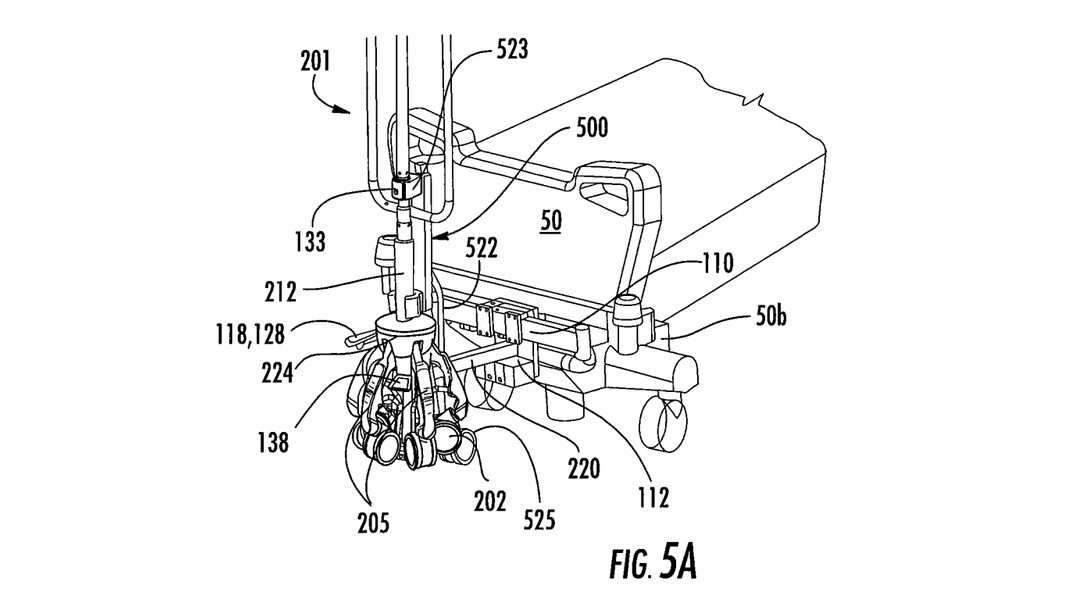
FIG. 5A is a side perspective view of a hospital bed-pole docking system with the wheels of the pole retracted according to embodiments of the present invention.
Figure 5B:
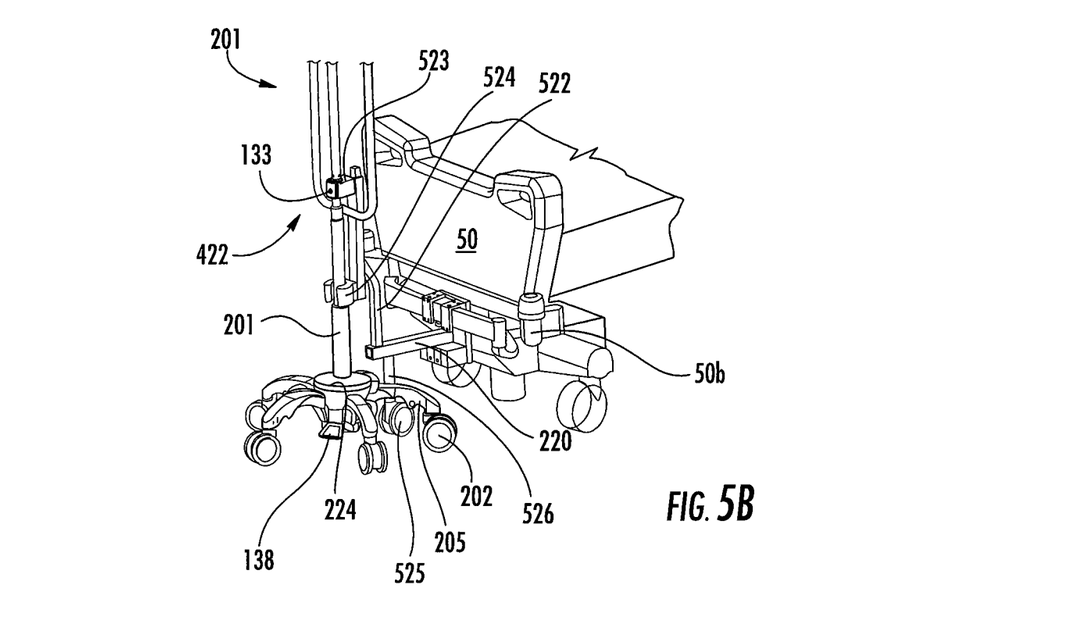
FIG. 5B is a side perspective view of the hospital bed-pole docking system shown in FIG. 5A with the legs of the pole extending and wheels on the ground ready for release from the hospital bed according to embodiments of the present invention.

FIGS. 5A and 5B illustrate that the pole (201) can be configured to serially, interchangeably dock to another device, shown as a base (50b) of a hospital bed (50), typically adjacent a headboard or foot board end of the bed. The bed docking system (500) can include an upwardly extending arm (522) that extends up from the base (50b) of the hospital bed and holds at least one pole attachment member (422), shown as upper and lower members (523), (524), similar to members (233), (234) discussed above for the boom interface. The key (133) can align with the upper mount member (523) and the narrower segment of the pole (213) can reside inside the upper mount member (523). Typically, the pole (201) is placed in the pole release position shown in FIG. 5A, then the foot pedal (138) is depressed to extend the legs (205) and place the wheels (202) on the floor as shown in FIG. 5B.

The bed docking system (500) can include a horizontal arm (220) that extends a distance out from the bed (50) and holds the upwardly extending arm (522) with the pole mounts (523), (524). The bed docking system (500) can also include a downwardly extending leg (526) with at least one wheel (525) that resides on the floor.

In some embodiments, the pole (10) of whatever use or uses including those described hereinabove, can be configured to be safely used in an MRI suite including in a magnetic field of an MRI Scanner. Thus, the pole (10) can be configured with non-ferromagnetic materials and components.

The terms "accessory" and "accessory devices" refer to any clinical or hospital device that may be desirable to be provided for and/or moved with a patient including poles such as IV poles, monitor supports, tables, trays, pump supports, oxygen tank/canisters and the like.

Although described with respect to an IV pole (201), the pole (201) may be configured for other uses. The term "transformable" when referring to some embodiments of the pole (201) means that the pole can transform between at least two different configurations, typically including a stowed configuration with the wheels (202) off of/above a support floor as shown in FIG. 4F and an extended configuration with the wheels (201) on the floor as shown in FIG. 1 with the wheels (205) able to provide a weight bearing support for the pole (202). The pole (201) can include a lift mechanism (203). The lift mechanism (203) can slide up and down relative to a medical portion of the pole (213). The legs (205) can pivot inward and outward relative to the mast (216) to be able to retract and extend the wheels (205) in the stowed and extended positions, respectively. The pole (201) can include at least one foot lever (128) for moving the legs/wheels between the stowed and extended positions. As shown, the pole (201) has a manually-actuated foot lever (128) in communication with the lift mechanism (203) for engaging an onboard (e.g., gas spring) actuator that raises the wheels (202). The pole (201) may also have a second lever for lowering the wheels (202) (not shown). The second lever can manually lower the wheels from force applied to the second lever. In some embodiments, the wheels (202) are caster-type wheels capable of freely rotating along a leg-wheel connection. Although in this particular depiction there are five legs (205) with five four-inch caster-type wheels (202), embodiments with different numbers of legs (such as 1, 2, 3 or 6 or more) and different sized or types of wheels, or combinations of different types or sizes, larger or smaller or combinations of different size wheels may be used.

The lift mechanism (203) may include a gas spring as described in U.S. Pat. No. 7,918,422, the contents of which are hereby incorporated by reference as if recited in full herein. Alternatively, other lift mechanisms including, for example, electric motor or pneumatic driven gears and/or links may be used.

In some embodiments, the legs can be moved between an extended configuration where the wheels contact a floor and a retracted configuration where the legs are drawn inward and the wheels are lifted to reside off the floor.

The poles can be configured for various purposes and/or provided as components of various devices. The poles can be an IV pole, an oxygen tank pole, a tray table pole, a monitor support pole, a pole attachable to a pediatric wagon, wheelchair or hospital bed or hospital beds with a pole docking system and/or any combination of the different uses and may be used for other hospital or care-based medical accessories.

The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

That which is claimed:

1. A method of engaging a pole to a boom in a room of a nursing home or medical facility, the method comprising:
rolling a pole with a mast coupled to a base and a plurality of circumferentially spaced apart outwardly extending legs, each leg holding at least one wheel supported by a floor;
aligning the pole with a downwardly extending arm of the boom, wherein the boom comprises at least one laterally extending arm that is coupled to the downwardly extending arm, and wherein the downwardly extending arm comprises a first pole attachment member and a second spaced apart pole attachment member residing under the first pole attachment member; then
attaching the pole into the first pole attachment member and the second pole attachment member; then
suspending or at least partially supporting the attached pole using the downwardly extending arm; then
manually engaging a foot pedal of the pole; and then
retracting the plurality of legs and lifting the at least one wheel of each leg off the floor in response to only the manually engaging action whereby the pole is suspended by the boom.

2. The method of claim 1, wherein the at least one wheel of each leg is above the base when retracted, and wherein the base is closer to the second pole attachment member after the pole is attached to the downwardly extending arm when the at least one wheel of each leg is retracted relative to when the pole is attached to the downwardly extending arm before the at least one wheel of each leg is retracted.

3. The method of claim 1, wherein the retracting is carried out to lift the base toward the first pole attachment member to lock the pole to the downwardly extending arm of the boom in response to the manually engaging action thereby providing a single user action to retract the legs, and lift and lock the pole to the downwardly extending arm of the boom.

4. The method of claim 1, wherein the at least one laterally extending arm is coupled to a central work station.

5. The method of claim 1, wherein the pole is an intravenous (IV) pole with a mast holding at least one IV bag attachment device.

6. The method of claim 1, wherein the pole comprises a plurality of concentric tubular segments residing above the base, including a first tubular segment having a diameter that is less than an adjacent second tubular segment, with a lower end portion of the second tubular segment attached to the base, and wherein the automatically retracting action is carried out by sliding the base and the second tubular segment upward, with the second tubular segment enclosing at least a portion of the first tubular segment.

7. The method of claim 6, further comprising rolling the pole across the floor toward a hospital bed and attaching the pole to an upwardly extending arm of a hospital bed docking interface after the pole is disengaged from the boom.

8. A boom with a one-step pole docking system comprising:
a boom with at least one laterally extending arm and a downwardly extending arm attached to the laterally extending arm, wherein the downwardly extending arm of the boom comprises at least one pole attachment member;
a transformable pole with a base comprising a plurality of circumferentially spaced apart outwardly extending legs, each leg holding at least one wheel, and a manual operated foot pedal, wherein the transformable pole has a first in-use configuration with the legs extended and the at least one wheel of each leg on the floor and a second stored configuration with the legs retracted inward toward the pole and the at least one wheel of each leg off the floor, and wherein the pole is releasably attachable to the at least one pole attachment member of the downwardly extending arm of the boom,
wherein the pole comprises first and second adjacent tubular pole segments extending above the base, wherein the first tubular segment is above the second tubular segment and has a smaller outer diameter than the second tubular segment, wherein the second tubular segment is attached to the base, wherein the first tubular segment is configured to releasably engage at least one of the at least one pole attachment member of the boom, and wherein the pole is automatically lifted to be suspended by the downwardly extending arm of the boom in response to manual engagement of the foot pedal by a user, once the first tubular segment of the pole is held by the at least one pole attachment member of the downwardly extending arm to thereby automatically retract the plurality of legs and lift the at least one wheel of each respective leg off a floor to be suspended by the boom in response to only the manually engaging action whereby the pole is suspended by the boom.

9. The system of claim 8, wherein the first tubular segment of the pole comprises an outwardly projecting key member, wherein the downwardly extending arm comprises a first pole attachment member and a second pole attachment member that is under the first pole attachment member and spaced apart in a longitudinal direction as the at least one pole attachment member, and wherein the first pole attachment member has a receiving channel with an open outer facing perimeter portion that releasably receives the first tubular segment of the pole so that the outwardly projecting key member couples to spaced apart arcuate segments of the first pole attachment member.

10. The system of claim 9, wherein the base of the pole resides a greater distance away from the first pole attachment member in the first in-use configuration than in the second stored configuration.

11. The system of claim 8, wherein the retraction and lifting of the legs self-locks the pole to the at least one pole attachment member of the downwardly extending arm of the boom.

12. The system of claim 8, wherein the pole is an intravenous (IV) pole and comprises a mast holding at least one IV bag attachment device.

13. The system of claim 8, wherein the pole has a key member that projects radially outward a distance from a portion of the first tubular segment of the pole.

14. The system of claim 13, wherein the key member is arcuate and extends radially outward from a segment of the pole for between 30-60 degrees of a perimeter of the first segment of the pole.

15. The system of claim 13, wherein the downwardly extending arm comprises a first pole attachment member and a second pole attachment member that is under the first pole attachment member and spaced apart in a longitudinal direction as the at least one pole attachment member, and wherein, with the first tubular segment attached to the first pole attachment member, the key member faces outward and abuts adjacent laterally extending arm segments of the first pole attachment member.

16. The system of claim 8, wherein the pole has a key member that is arcuate and extends radially outward from the first tubular segment of the pole, wherein the at least one pole attachment member comprises first and second attachment members, and wherein the key member aligns with the first pole attachment member to lockingly engage the pole.

17. The system of claim 8, wherein the downwardly extending arm can rotate about a pivot axis, and wherein the at least one laterally extending arm can rotate about at least one vertical pivot axis.

* * * * *